United States Patent [19]

Sivilich

[11] Patent Number: 4,589,877

[45] Date of Patent: May 20, 1986

[54] MALE INCONTINENCE DEVICE

[75] Inventor: Daniel M. Sivilich, Freehold Township, Monmouth County, N.J.

[73] Assignee: E. R. Squibb & Sons, Inc., Princeton, N.J.

[21] Appl. No.: 749,598

[22] Filed: Jun. 27, 1985

Related U.S. Application Data

[63] Continuation-in-part of Ser. No. 644,610, Aug. 27, 1984, abandoned.

[51] Int. Cl.⁴ ............................................. A61F 13/16
[52] U.S. Cl. ............................................. 604/385 R
[58] Field of Search .................... 604/368, 385–389, 604/394–400; 2/403, 404, 405

[56] References Cited

U.S. PATENT DOCUMENTS

| | | |
|---|---|---|
| 2,699,170 | 1/1955 | Morin . |
| 2,896,627 | 7/1959 | Harwood . |
| 3,072,123 | 1/1963 | Davis . |
| 3,183,910 | 5/1965 | Patterson . |
| 3,211,147 | 10/1965 | Pherson et al. . |
| 3,315,676 | 4/1967 | Cooper . |
| 3,344,789 | 10/1967 | Arnold et al. . |
| 3,431,911 | 3/1969 | Meisel, Jr. . |
| 3,570,492 | 3/1971 | Bettencourt . |
| 3,666,611 | 5/1972 | Joa . |
| 3,707,430 | 12/1972 | Costanza et al. . |
| 3,769,978 | 11/1973 | De Night et al. . |
| 3,868,287 | 2/1975 | Lewyckyj . |
| 3,871,037 | 3/1975 | Willington . |
| 3,890,974 | 6/1975 | Kozak . |
| 3,897,784 | 8/1975 | Fitzgerald . |
| 3,938,522 | 2/1976 | Repke . |
| 4,002,171 | 1/1977 | Taft . |
| 4,027,672 | 6/1977 | Karami . |
| 4,055,180 | 10/1977 | Karami . |
| 4,055,184 | 10/1977 | Karami . |
| 4,085,754 | 4/1978 | Ness et al. . |
| 4,093,765 | 6/1978 | Schmidt . |
| 4,372,309 | 2/1983 | Fowler . |

Primary Examiner—John D. Yasko
Attorney, Agent, or Firm—Lawrence S. Levinson; Robert E. Lee, Jr.

[57] ABSTRACT

A method and apparatus for providing a male incontinence shield for use with a user's undergarment including partially overlapping inner and outer moisture absorbent pad portions coupled together at opposite ends whereby a penile opening is formed to allow normal urination for the lightly incontinent male. Each pad portion comprises an absorbent core with a first relatively thick absorbent portion and a layer of super absorbent material which gels immobilizing the absorbed liquid. A cover encloses the core comprising a moisture permeable body side section and a moisture impermeable garment side section. In one embodiment, for the inner pad portion, the moisture permeable section extends around one side of the pad to form a portion of the garment side section in the region of overlap. Adhesive means attached to the garment side of the shield are provided for securing the shield to the undergarment. In a preferred method of manufacture, a moisture permeable sheet of material is sealed to a moisture impermeable sheet along a top edge and longitudinal center portion extending away from the top edge. Moisture absorbent cores are placed between the sheets on either side of the center portion and a slit is placed in the sheets in the center portion. The sheets are sealed together at least partially around the remaining periphery of the cores. One core is partially folded over the other and the combination heat sealed along top and bottom edges. The excess sheet material is trimmed off along the peripheral sealing lines to form the shield.

31 Claims, 11 Drawing Figures

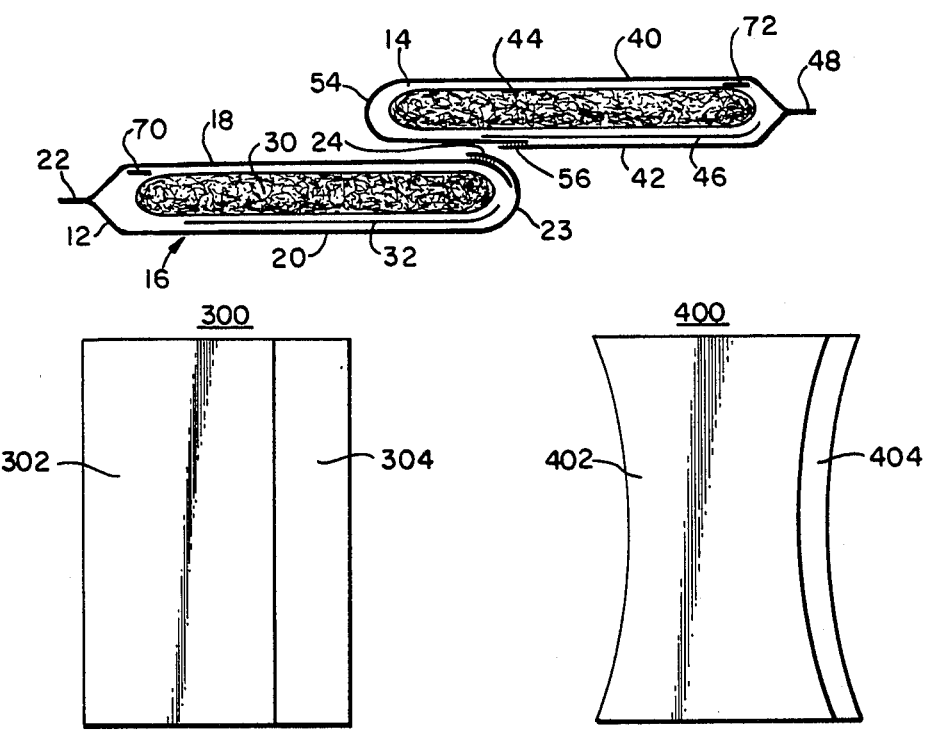
FIG. 2
FIG. 3
FIG. 4
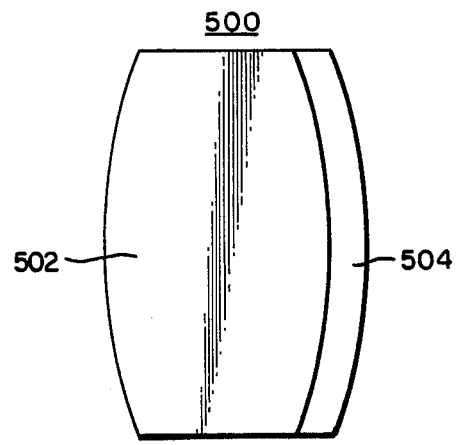
FIG. 5

MALE INCONTINENCE DEVICE

This is a continuation-in-part of co-pending application Ser. No. 644,610 filed on Aug. 27, 1984, now abandoned.

BACKGROUND OF THE INVENTION

The present invention relates to moisture absorbant pads, and, more particularly, to an improved moisture absorbent shield for use by male incontinence patients and the method of making same.

Incontinence is a malody from which a great many elderly and ill individuals suffer. The inability to restrain or control the discharge of waste material from the body, particularly urine, is a problem which often cannot be remedied and, therefore, it is necessary to provide the incontinent individual with a means for containing the discharge, thereby enabling the individual to lead a relatively normal life.

One successful approach to this problem has been the use of incontinence garments such as briefs or the like, which can be used and reused. Such garments are provided with a pocket-like structure into which a disposable moisture absorbent incontinence pad can be inserted. The pad, once it becomes moisture laden, is removed from the garment and a new pad is substituted in its place. Alternatively, a disposable incontinence pad is provided which is adapted for use with normal underclothing and is attached or fixed thereto by strips of adhesive tape or other suitable means.

However, for lightly incontinent males the above described pads are an impediment to normal urination. A pad is required for such individuals but one which is adapted to accomodate normal urination as well.

SUMMARY OF THE INVENTION

An object of the invention is to provide an improved moisture absorbing shield for the lightly incontinent male.

Accordingly, a male incontinence shield is provided which includes inner and outer moisture absorbing pad portions which are coupled together at opposite ends and which only partially overlap to form a penile opening. Each pad portion comprises a moisture absorbent core portion and a cover surrounding the core. The cover comprises a body side moisture permeable section and a garment or outer side moisture impermeable section. In one embodiment the liquid permeable section of the cover of the inner pad portion extends around one side of the cover of the inner pad to form a portion of the garment side of the inner pad portion and which faces the liquid permeable section of the cover of the outer pad portion in the overlap region between the two pad portions.

The absorbent core comprises a first relatively thick liquid absorbent portion and a second super absorbent layer for immobilizing absorbed liquid. The super absorbent layer is disposed between the first absorbent portion and the impermeable cover section of the pad. In one embodiment the super absorbing layer of the inner pad portion terminates before extending into the overlap region.

The super absorbent layer comprises a laminant of a base or carrier and a polymer which gels when wet. A polymer may be either a starch polymer, an acyrlic polymer, a modified cellulose polymer, etc.

The relatively thick absorbent portion of the moisture absorbing core preferably is made of a fluffed wood pulp, while the moisture permeable section of the cover comprises a non-woven fibrous material. The moisture impermeable section can be either polyethylene or polypropylene film, for example.

The shield further comprises an adhesive means which is attached to the garment side of the shield for securing the shield to the user's undergarment. In addition to being sealed at opposite ends, the pad portions are additionally coupled together by coupling the outer cover section of the inner pad portion to the body side cover section of the outer pad portion along a region extending away from both the top and bottom ends.

The invention further comprises the method of making the above described male incontinence shield comprising coupling inner and outer partially overlapping moisture absorbing pad portions at opposite ends to form a penile opening. The method further comprises providing pressure sensitive adhesive strips near the opposite ends of the shield on the garment side for securing the shield to the user's under-garment. Further, the pad portions are formed by enclosing a moisture absorbent core portion with a cover having a body side moisture permeable section and a garment side moisture impermeable section. In one embodiment the body side moisture permeable section of the inner pad is wrapped around one side of the inner pad to form a portion of the garment side of the inner pad in the overlapping region.

In the preferred method of making the shield two moisture absorbing cores are sealed at least around a portion of their perimeters between moisture permeable and moisture impermeable sheets to form two pad portions. A longitudinal slit is made in the sheets between the cores and one pad portion is folded partially over the other. The pad portions are then sealed together along their top and bottom edges. Sealing is accomplished using heat, ultrasound or glue.

In one method of sealing the cores between the moisture permeable and impermeable sheets, the sheets are first sealed together along a top edge and along a center portion which extends longitudinally away from the top edge. The cores are inserted between the sheets on either side of the center portion and the sheets are sealed together at least on opposite sides of the cores from the center portion. The center portion may be sealed along two parallel and spaced apart lines and the slit made between the lines.

BRIEF DESCRIPTION OF THE DRAWINGS

FIG. 2 is a cross-section of the device of FIG. 1 taken along the lines and arrow 2—2.

FIG. 3 shows a first alternate shape of the device of FIG. 1 in reduced size.

FIG. 4 shows a second alternate shape of the device of FIG. 1 in reduced size.

FIG. 5 shows a third alternate shape of the device of FIG. 1 in reduced size.

DETAILED DESCRIPTION OF THE DRAWINGS

Figure 1:
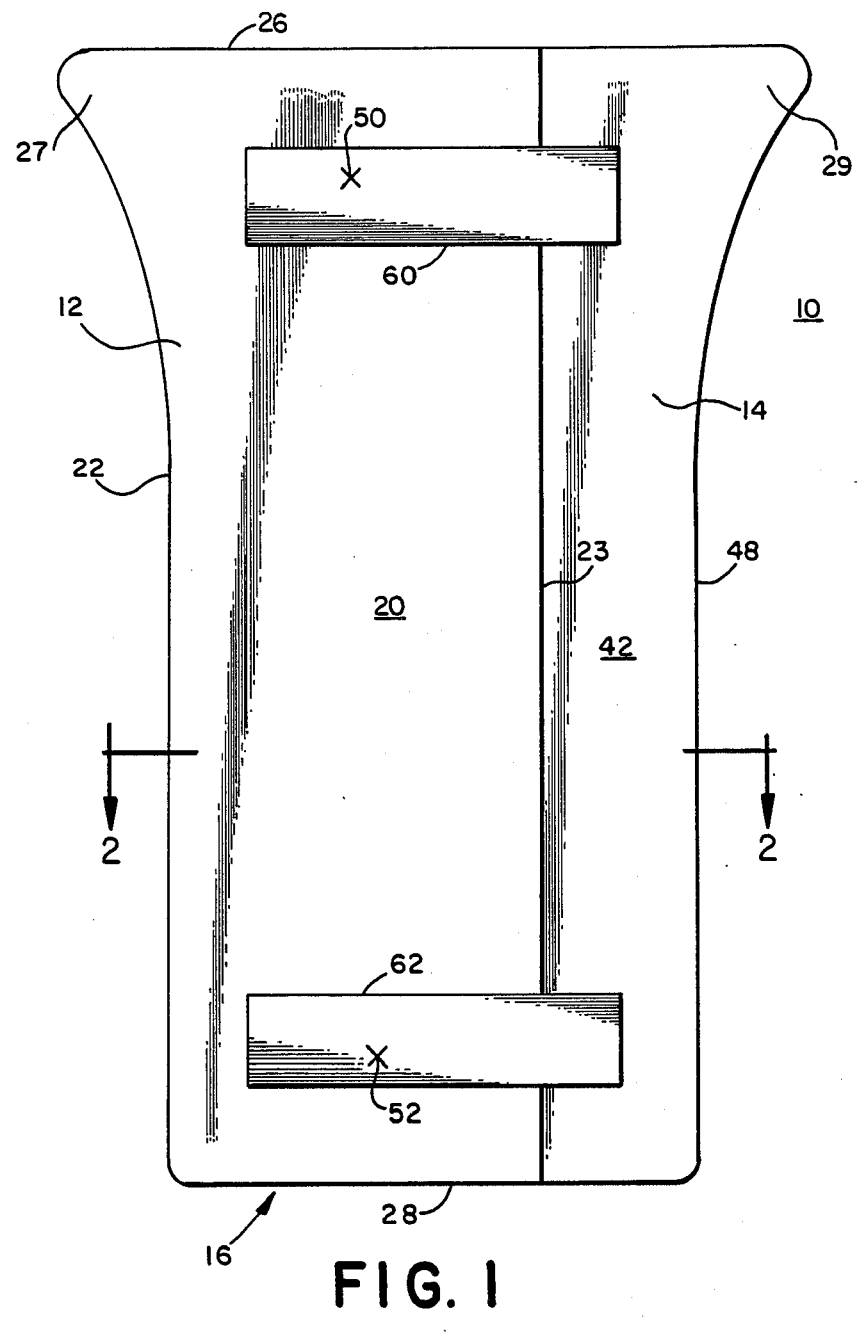
FIG. 1 is a planar view of an embodiment of the male incontinence device of the present invention.

Referring now to FIGS. 1 and 2, the improved male incontinence device designated generally 10 comprises partially overlapping incontinence pads 12 and 14. Each of the pads has similar construction. For example, outer pad 12 has a cover 16 formed of a moisture permeable body side section 18, and a moisture impermeable garment side section 20. Moisture permeable section 18 is composed of non-woven material made of polyester, polypropylene, or rayon fibers, or the like, which permit the passage of fluid therethrough. The moisture permeable sector 20 is preferably formed of polyethylene or polypropylene or the like.

The permeable section 18 of the cover 16 for pad 12 is joined to the impermeable section 20 along the left edge 22 and the top and bottom edges 26 and 28, respectively. At the right end 23 of pad 12 the impermeable section 20 wraps around the right end and is joined to the permeable section along line 24. Joining is accomplished by adhesives, heat sealing, ultrasonic sealing, etc.

The preferred embodiment pad is shaped with an outwardly extending portion at one end on the outer side of the pad. See the portions 27 for pad 12 and 29 for pad 14.

The sections 18 and 20 surround a relatively thick layer of moisture absorbent core material 30, such as fluffed wood pulp, tissue-wadding foams, non-wovens, batting, cellulosic fibers, rayon poly acrylate, cotton or the like, and a relatively thin layer of a super absorbent polymer 32. The super absorbent polymer 32 is situated between core 30 and the garment side moisture impermeable section 20. Liquid passing through the permeable body side section 18 of the cover 16 is taken up by core 30 and passed onto the super absorbent polymer layer 32 which gels when wet and immobilizes the liquid.

Super absorbent polymer layer 32 may be one or more sheets of material. Preferred materials for the layer 32 are a laminate containing a super absorbent starch polymer known as DWAL (trademark of Dow Chemical) or a laminate containing a super absorbent modified acrylic polymer known as Gelok 4000 (trademark of Gelok International). Alternatively, the super absorbent can also be in a powder or granule form sprinkled or laid in as a layer.

Inner pad 14, like pad 12, comprises a body side moisture permeable section 40, a garment side moisture impermeable section 42, and an absorbent core material 44 and super absorbent layer 46. The top and bottom ends of the two pads 12 and 14 are coupled together by any suitable process such as heat sealing, hot melt adhesives, etc., to form a single unit. The pads are offset when the ends are sealed to one another thus forming an area of partial overlap between the two pads. This can be seen in FIG. 1 where right side 23 of pad 12 is offset from the right side 48 of pad 14. In the preferred embodiment the overlap area between the two pads is approximately two inches.

The pads 12 and 14 can be additionally secured to one another near the top and bottom edges in the overlap region by using adhesives, e.g., hot melt, latex, etc., or by heat or ultrasonic sealing depending on the materials chosen for the cover. In one embodiment, the pads were additionally secured by using a one inch long hot melt adhesive strip positioned at the locations denoted by X's 50 and 52 in FIG. 1 between opposing surfaces of the two pads in the overlap region.

Section 40 of pad 14 is sealed to section 42 along the outer edge 48 of the pad 14 in a manner similar to the edge 22 of pad 12. Section 40 wraps around the inner edge 54 of pad 14 and is sealed to section 42 along line 56. This arrangement allows moisture to pass from inner pad 14 through the portion of moisture permeable section 40 facing the overlapping portion of moisture permeable section 18 on outer pad 12, and then through section 18 into the pad 12. It should be noted as well that the super absorbent polymer layer 46 of pad 14 does not extend into the overlap area. This arrangement facilitates movement of moisture from the inner pad 14 to the outer pad 12 and away from the body of the wearer. The extension of impermeable section 20 around edge 23 of pad 12 prevents liquid or moisture which may accumulate there from dripping from the pad. However, section 20 does not extend so far around as to prevent moisture from moving from pad 14 into pad 12 in the manner described above.

Referring now to FIG. 1, strips of pressure sensitive adhesive 60 and 62 are attached to the garment side of the shield 100 near the top and bottom, respectively, of the pads 12 and 14. The pressure sensitive adhesive may be double face tape for example.

The shield is secured to the user's undergarment using the adhesive strips. The penile opening of the shield formed by the overlap between pads 12 and 14 is aligned with the penile opening of the undergarment. In place the shield absorbs any discharge protecting the user's garments.

However, should the user desire to urinate normally, he can do so through the penile openings of the pad and undergarment.

While FIG. 1 shows the preferred embodiment shape of the shield, alternate shapes are shown in FIGS. 3, 4 and 5. FIG. 3 shows a shield 300 made from two rectangular pads 302 and 304; FIG. 4 shows a shield 400 made from two partially oval pads 402 and 404; and FIG. 5 shows a shield 500 made from pads having double concave sides 502 and 504.

The shield can be formed using elastomeric polymer strips 70 and 72 as in FIG. 2 on the outer sides of the inner and outer pads forming the shield. The strips can be centrally located between the top and bottom of each pad or formed to run the entire length of the outer side of each pad.

Figure 6:
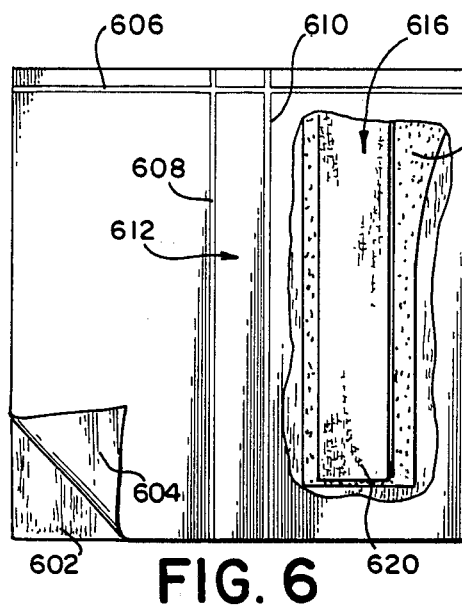
FIG. 6 shows the male incontinence device of the present invention during an initial step of manufacture showing one of the absorbing cores inserted between the cover sheets of the device through a break away.

A preferred method of making a male incontinence shield with a penile opening will now be described with respect to FIGS. 6–11. In FIG. 6 a moisture permeable body side sheet 602 similar to the section 18 in FIG. 2, such as a light weight (0.5 oz. per sq. yd) non woven fabric of polyester of polyethylene, is provided along with a moisture impermeable garment side sheet 604 which is similar to the moisture impermeable section 20 of FIG. 22, such as a 0.6 mil polyethylene or polypropylene film. The two sheets are joined or sealed together along a top edge 606 and along two parallel and spaced apart lines 608 and 610 in a center portion 612 of the sheets which extends longitudinally from the top edge 606. FIG. 6 shows a corner of the sheet 604 folded up to expose the sheet 602.

A moisture absorbent core 616 is inserted between the sheets 602 and 604 on either side of the center portion 612. A portion of sheet 604 is shown broken away on the right hand side of FIG. 6 to expose the core 616 which in the preferred embodiment comprises one or more layers of moisture absorbent material 618 comprising fluff pulp, absorbent fibers, absorbent wadding etc., similar to core 30 in FIG. 2, and one or more layers of a super absorbent material 620 similar to polymer 32 in FIG. 2. In the preferred embodiment the layers 618 are on the body side and the layers 620 on the garment side.

Figure 7:
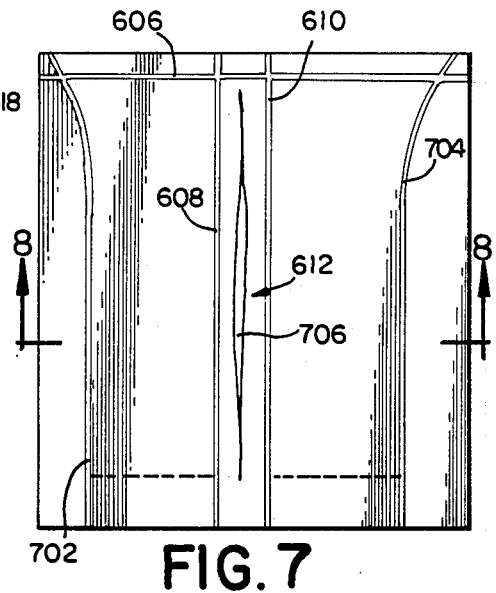
FIG. 7 shows the male incontinence device of the present invention in a further stage of manufacture with a longitudinal slit placed in the cover sheets between the absorbing cores.

Once the cores 616 of absorbing material are placed between the cover sheets 602 and 604 on either side of center portion 612, the cover sheets are sealed at least partially around the remaining periphery of the cores, e.g., at side edges 702 and 704 in FIG. 7. Then a longitudinal slit 706 is placed in the sheets in the center portion 612 between the sealing lines 608 and 610. In the preferred embodiment the slit is approximately ¼ inch from the inner seal 608.

Figure 8:
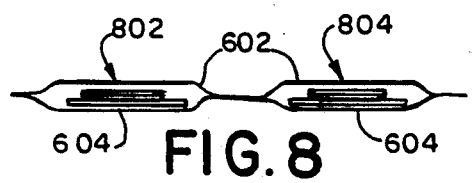
FIG. 8 is a cross sectional view of the shield of FIG. 7 taken along the lines and arrows 8—8 in FIG. 7.
Figure 10:
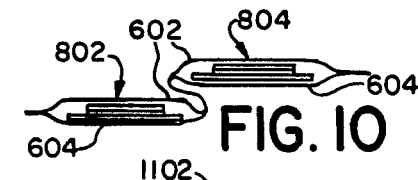
FIG. 10 is a cross sectional view of the shield of FIG. 9 taken along the lines and arrows 10—10 in FIG. 9.
Figure 9:
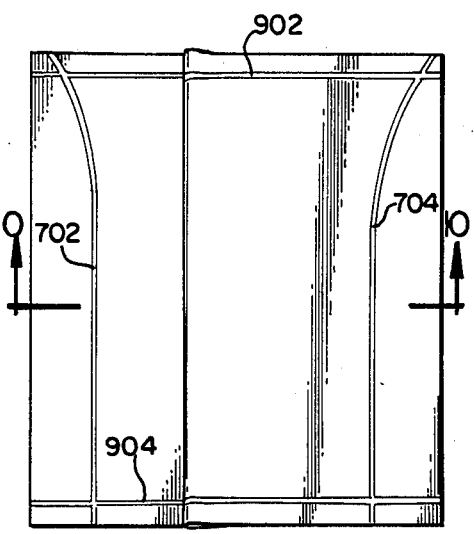
FIG. 9 shows the male incontinence device of the present invention in still a further stage of manufacture with one pad portion partially folded over the other.
Figure 11:
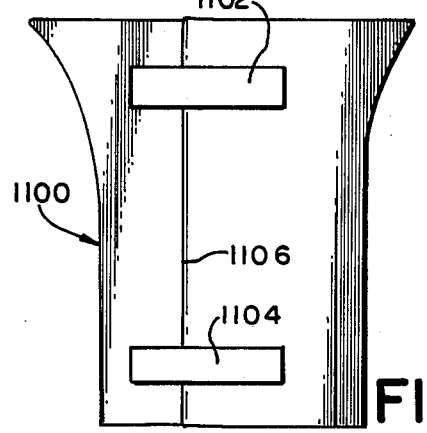
FIG. 11 is a planar view of the preferred embodiment male incontinence device of the present invention resulting from the manufacturing steps of FIGS. 6–10.

FIG. 8 is a cross section of the shield taken along the lines and arrows 8—8 in FIG. 7 showing side by side pad portions designated generally 802 and 804. Referring to FIG. 10, one of the pad portions e.g., pad portion 804, is next folded partially over the other pad portion with the moisture permeable sheet 602 always positioned on the body side of the shield and the moisture impermeable sheet 604 on the garment side. The distance of crossover or overlap is proportional to the distance between the two pad portions 802 and 804. In the preferred embodiment, the distance of overlap is ⅜ inch. A portion of the moisture impermeable sheet covering the core of the pad portion 804 faces a portion of the moisture permeable sheet covering the core of the pad portion 802 as in FIG. 10.

After the pad portions have been folded over as just described the top edge of the overlapping pad portions are sealed together along their common top edge 902 which usually overlaps or is near the sealing line 606. The pad portions are sealed along their common bottom edge at 904. Then the overall shield is trimmed along the peripheral sealing edges 702, 902, 704 and 904 to form the shield 1100 in FIG. 11. Two or more adhesive strips 1102 and 1104 are placed on the moisture impermeable sheet to secure the shield to the user's undergarment while in use. These adhesive strips can be pressure sensitive hot melt/release paper, water or solvent based pressure sensitive adhesive/release paper, or double sided tape. In the preferred embodiment a pressure sensitive hot melt is used. The final shield can be opened along line 1106.

The sealing step described for FIGS. 6-11 can be heat sealing, ultrasonic welding, glueing or the like.

I claim:

1. A male incontinence shield for use with a user's undergarment comprising:
    inner and outer moisture absorbent pad portions coupled together at opposite ends and partially overlapping one another to form a penile opening.
2. The shield of claim 1 wherein each pad portion comprises:
    a moisture absorbent core portion; and
    a cover surrounding said core portion, said cover comprising a body side moisture permeable section and an outer moisture impermeable section.
3. The shield of claim 2 wherein said body side liquid permeable section of said inner pad portion extends around one side of said inner pad portion to face the liquid permeable section of said outer pad portion in a region formed by said overlapping.
4. The shield of claim 1 wherein said shield comprises adhesive means attached to the garment side of said shield for securing said shield to the user's undergarment.
5. The shield of claim 3 wherein said shield comprises adhesive means attached to the garment side of said shield for securing said shield to the user's undergarment.
6. The shield of claim 3 wherein said core portion of each pad portion comprises:
    a first relatively thick absorbent portion; and
    a super absorbent layer for immobilizing absorbed liquid disposed between said first absorbent portion and said moisture impermeable section, the super absorbent layer of said inner pad portion terminating before extending into said overlapping region.
7. The shield of claim 6 wherein said super absorbent layer comprises a laminate of a base or carrier and a polymer which gels when wet.
8. The shield of claim 7 wherein said polymer is a starch polymer.
9. The shield of claim 7 wherein said polymer is an acrylic polymer.
10. The shield of claim 6 wherein said super absorbent layer comprises a super absorbent powder or granules.
11. The shield of claim 2 wherein said moisture permeable section comprises a non-woven fibrous material.
12. The shield of claim 2 wherein said moisture impermeable section is a polyethylene film.
13. The shield of claim 6 wherein said relatively thick absorbent portion is fluffed wood pulp.
14. The shield of claim 2 wherein said pad portions are additionally coupled together by coupling the outer cover section of said inner pad portion to the body side cover section of said outer pad portion along a region extending away from said opposite ends.
15. The shield of claim 1 wherein said inner and outer pad portions are rectangularly shaped.
16. The shield of claim 1 wherein said inner and outer pad portions are oval pad portions.
17. The shield of claim 1 wherein said inner and outer pad portions have double concave shaped sides.
18. The shield of claim 1 wherein said shield further comprises an elastomeric polymer strip attached to the outer side of each of said inner and outer pad portions.
19. A method of making a male incontinence shield for use with a user's undergarment comprising:
    coupling inner and outer partially overlapping moisture absorbing pads at opposite ends to form a penile opening.
20. The method of claim 19 wherein said method further comprises providing pressure sensitive adhesive strips near the opposite ends of said shield for securing said shield to said user's undergarment.
21. The method of claim 20 wherein said method further comprises:
    enclosing a moisture absorbing core portion with a cover having a body side moisture permeable section and a garment side moisture impermeable section to form said inner and outer pads.

22. The method of claim 21 wherein said method further comprises/wrapping said body side moisture permeable section around one side of said inner pad to cover a portion of said garment side section of said inner pad in the region where the pads overlap.

23. A method of making a male incontinence shield for use with a user's undergarments comprising the steps of:
- sealing two moisture absorbing cores around at least a portion of their perimeters between a moisture permeable body side sheet and a moisture impermeable garment side sheet to form two pad portions;
- making a longitudinal slit in said sheets between said pad portions;
- folding one of said pad portions partially over th remaining one of said pad portions, keeping the moisture permeable sheet of said pad portions facing the body side and the moisture impermeable sheet of said pad portions facing the garment side; and
- sealing said overlapping pad portions together along top and bottom edges.

24. The method of claim 23 wherein said sealing steps comprise heat sealing.

25. The method of claim 23 wherein said sealing steps comprise ultrasonic welding.

26. The method of claim 23 wherein said sealing steps comprise glueing.

27. The method of claim 23 wherein the step of sealing two pad portions around at least a portion of their perimeters comprises:
- sealing said sheets together along a top edge thereof and along a center portion thereof extending longitudinally away from said top edge;
- inserting said pads between said sheets on either side of said center portion; and
- sealing said sheets together on opposite sides of said cores from said center portion.

28. The method of claim 27 wherein the step of sealing said sheets together along a center portion comprises sealing said sheets together along substantially parallel and spaced apart lines and wherein said longitudinal slit is made between said lines.

29. The method of claim 23 wherein the method further comprises the step of trimming said shield along the sealed perimeter of said folded over and sealed together pad portions.

30. The method of claim 23 wherein said method further comprises the step of providing pressure sensitive adhesive strips near the opposite ends of said shield for securing said shield to said user's undergarment.

* * * * *